United States Patent
Um et al.

(10) Patent No.: US 9,163,048 B2
(45) Date of Patent: Oct. 20, 2015

(54) MULTI-FUNCTIONAL NUCLEIC ACID-BASED ANTI-CANCER DRUG CAPABLE OF TARGETING AND THERAPY, METHOD FOR PREPARING SAME AND ANTI-CANCER COMPOSITION COMPRISING SAME

(71) Applicant: RESEARCH & BUSINESS FOUNDATION SUNGKYUNKWAN UNIVERSITY, Suwon-si (KR)

(72) Inventors: Soong Ho Um, Seoul (KR); A Ra Kim, Suwon-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 14/352,211

(22) PCT Filed: Sep. 21, 2012

(86) PCT No.: PCT/KR2012/007603
§ 371 (c)(1),
(2) Date: Apr. 16, 2014

(87) PCT Pub. No.: WO2013/058482
PCT Pub. Date: Apr. 25, 2013

(65) Prior Publication Data
US 2014/0350230 A1  Nov. 27, 2014

(30) Foreign Application Priority Data
Oct. 17, 2011 (KR) ........................ 10-2011-0105947

(51) Int. Cl.
| | | |
|---|---|---|
| *A61K 47/48* | (2006.01) | |
| *C12N 15/113* | (2010.01) | |
| *C07H 1/06* | (2006.01) | |
| *C07H 15/252* | (2006.01) | |

(52) U.S. Cl.
CPC .............. *C07H 1/06* (2013.01); *A61K 47/4813* (2013.01); *A61K 47/48861* (2013.01); *A61K 47/48884* (2013.01); *C07H 15/252* (2013.01)

(58) Field of Classification Search
None
See application file for complete search history.

(56) References Cited

U.S. PATENT DOCUMENTS

| | | | |
|---|---|---|---|
| 2009/0197261 A1* | 8/2009 | Lu et al. ............................ | 435/6 |
| 2011/0178161 A1 | 7/2011 | Trent et al. | |
| 2011/0237652 A1 | 9/2011 | Weiss et al. | |
| 2012/0141382 A1* | 6/2012 | Shi et al. .................... | 424/9.323 |
| 2012/0141550 A1* | 6/2012 | Maye et al. .................. | 424/400 |

FOREIGN PATENT DOCUMENTS

| | | |
|---|---|---|
| KR | 10-2008-0007323 A | 1/2008 |
| KR | 10-2011-0050338 A | 5/2011 |

OTHER PUBLICATIONS

Frederick, Christine A., et al. "Structural Comparison of Anticancer Drug—DNA Complexes: Adriamycin and Daunomycin". Biochemistry, vol. 29 (1990): 2538-2549.

Farokhzad, Omid C., et al."Nanoparticle-Aptamer Bioconjugates: A New Approach for Targeting Prostate Cancer Cells". Cancer Research, vol. 64 (2004): 7668-7672.

Huang, Chih-Ching et al. "Aptamer-Modified Gold Nanoparticles for Colorimetric Determination of Platelet-Derived Growth Factors and Their Receptors". Analytical Chemistry. vol. 77 No. 17 (2005): 5735-5741.

Huang, Yu-Fen et al. "Aptamer-modified gold nanoparticles for targeting breast cancer cells through light scattering". Journal of Nanoparticle Research. vol. 11, No. 4 (2009): 775-783.

International Search Report mailed Feb. 28, 2013 in counterpart International Application No. PCT/KR2012/007603 (2 pages, in English).

* cited by examiner

*Primary Examiner* — Tracy Vivlemore
(74) *Attorney, Agent, or Firm* — NSIP Law

(57) ABSTRACT

The present invention relates to a multi-functional nucleic acid-based anti-cancer drug in which the anti-cancer drug is physically bound to a linear nucleic acid having a thiol group at 5' terminal thereof and then gold nanoparticles and aptamers are chemically bound. The present invention also relates to a method for preparing the anti-cancer drug and to an anti-cancer composition comprising the anti-cancer drug. The multi-functional nucleic acid-based anti-cancer drug according to the present invention uses A10 aptamer to achieve high targeting properties, and uses high-concentration anti-cancer drugs and gold nanoparticles to enable dual therapy of thermal therapy/chemical therapy, and may have less side effects and be more effective in anti-cancer therapy compared to existing anti-cancer drugs.

10 Claims, 8 Drawing Sheets

MULTI-FUNCTIONAL NUCLEIC ACID-BASED ANTI-CANCER DRUG CAPABLE OF TARGETING AND THERAPY, METHOD FOR PREPARING SAME AND ANTI-CANCER COMPOSITION COMPRISING SAME

CROSS-REFERENCE TO RELATED APPLICATIONS

This application is a National Stage of International Application No. PCT/KR2012/007603, filed Sep. 21, 2012 and published as WO2013/058482 on Apr. 25, 2013, which claims the benefit of Korean Patent Application No. 10-2011-0105947, filed on Oct. 17, 2011, the entire disclosures of which are incorporated herein by reference for all purposes.

SEQUENCE LISTING

The instant application contains a Sequence Listing which has been submitted electronically in ASCII format and is hereby incorporated by reference in its entirety. Said ASCII copy, created on Jul. 9, 2014, is named 042099.0010_SL.txt and is 1,841 bytes in size.

TECHNICAL FIELD

The present invention relates to a multifunctional nucleic-acid-based anticancer drug prepared by chemically binding gold nanoparticles, an aptamer and an anticancer drug to a linear nucleic acid having a thiol group at the 5' end, a method of manufacturing the same, and an anticancer drug composition having the same.

BACKGROUND ART

Conventional anticancer drugs are introduced into various metabolic pathways of cells in which division is actively progressing, and most of them exhibit anticancer activity by inhibiting synthesis of a nucleic acid or generating cytotoxicity. However, the drugs did not selectively act only on cancer cells, but also damaged normal cells, particularly those of tissues that were actively dividing, resulting in serious side effects such as nausea, gastroenteric trouble, alopecia, leukopenia caused by myelosuppression, etc.

Accordingly, recently, various studies for developing an anticancer drug having a targeting property that can minimize damage to normal cells are progressing. According to the progress of such studies, studies on the development of various targeting anticancer drugs such as a manual targeting method in which an anticancer drug is accumulated only in cancer cells having abnormal blood vessels, the development of an anticancer drug using siRNA inhibiting expression of a specific gene, and the development of an anticancer drug using various peptides or nucleic acid aptamers binding to specific cancer cells are actively progressing. However, such targeting anticancer drugs still have problems in terms of low anticancer effects, low targeting properties, and complicated preparation methods.

Meanwhile, since a cancer is a complicated disease in which various mechanisms operate, and thus is unlikely to be completely cured using only one method such as chemotherapy using anticancer drugs or radiotherapy, recently, attention to anticancer treatment through integrating various treatments is increasing. However, there is still a lack of studies on multifunctional anticancer drugs.

For such effective anticancer treatment, there is a demand for the development of a multifunctional anticancer drug having a high targeting property, a high anticancer effect and an easy preparation method.

DISCLOSURE

Technical Problem

The present invention is directed to providing a multifunctional nucleic-acid-based anticancer drug to which a nucleic acid, gold nanoparticles and an anticancer drug having a high targeting property and a high anticancer effect are bound, a method of preparing the same, and an anticancer drug composition including the same.

However, technical objects to be performed in the present invention are not limited to the above-described object, and other objects that are not described will be fully understood by those of ordinary skill in the art from the following descriptions.

Technical Solution

In one aspect of the present invention, a multifunctional nucleic-acid-based anticancer drug prepared by chemically binding gold nanoparticles, and a nucleic acid aptamer after an anticancer drug is physically captured in a linear nucleic acid having a thiol group at the 5' end is provided.

In one embodiment of the present invention, the linear nucleic acid is composed of a combination of DNA sequences represented by SEQ. ID. NOs: 1 and 2.

In another embodiment of the present invention, the nucleic acid aptamer has a cancer cell targeting property.

In still another embodiment of the present invention, the nucleic acid aptamer is an A10 aptamer selectively binding to prostate cancer cells.

In yet another embodiment of the present invention, the anticancer drug has an aromatic ring.

In yet another embodiment of the present invention, the anticancer drug is doxorubicin.

In another aspect of the present invention, a method of preparing a multifunctional nucleic-acid-based anticancer drug includes (a) capturing an anticancer drug in a linear nucleic acid having a thiol group at the 5' end, (b) forming an anticancer-drug-captured nucleic acid structure by binding a nucleic acid aptamer having a targeting property to the linear nucleic acid, and (c) binding gold nanoparticles to the anticancer-drug-captured nucleic acid structure.

In one embodiment of the present invention, in the step (a), an aromatic ring of the anticancer drug is inserted into a sequence of the liquid nucleic acid.

In another embodiment of the present invention, the step (b) is performed by binding of complementary sequences of the liquid nucleic acid and the nucleic acid aptamer.

In still another embodiment of the present invention, the step (c) is performed by a covalent bond between the thiol group and the gold nanoparticles of the anticancer-drug-captured nucleic acid structure.

In still another aspect of the present invention, a pharmaceutical composition including an effective amount of the multifunctional nucleic-acid-based anticancer drug is provided.

In one embodiment of the present invention, the composition is used to treat prostate cancer.

Advantageous Effects

A multifunctional nucleic-acid-based anticancer drug according to the present invention is a nano-level structure formed by a bond of a nucleic acid, an anticancer drug, and gold nanoparticles, which can deliver the anticancer drug into specific cells through a nucleic acid aptamer having a targeting property and stimulate thermal treatment and release of the anticancer drug by the gold nanoparticles. The multifunctional nucleic-acid-based anticancer drug of the present invention is expected to have a high targeting property, minimize an effect on normal cells since the anticancer drug is captured by a linear nucleic acid, have a more excellent therapeutic effect than a conventional anticancer drug through dual therapy of thermal treatment/chemotherapy, and thus reduce a dosage of a drug and the number of administrations of the drug. In addition, because a nucleic acid aptamer or chemical having a targeting property suitable for treating various diseases is introduced into the multifunctional nucleic-acid-based anticancer drug without limitation, it is expected to be source technology capable of being applied to treatment of various intractable diseases.

MODES OF INVENTION

Figure 1:
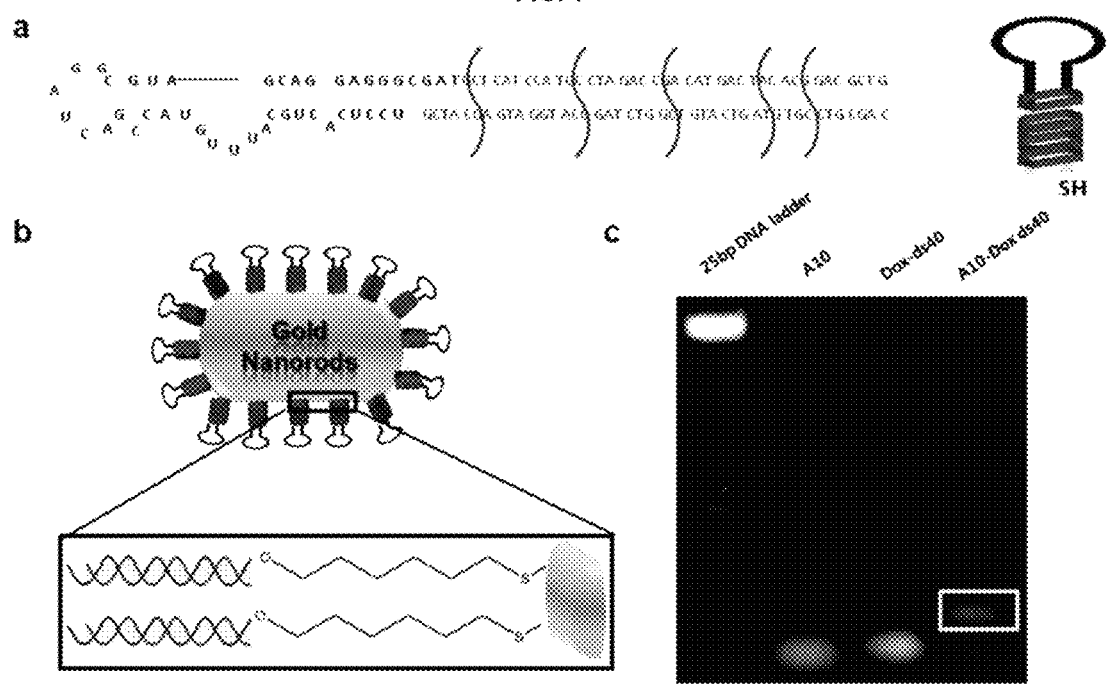
FIG. 1 shows (a) a schematic diagram of a nucleic acid structure (SEQ ID NO: 4) in which an anticancer drug is captured, (b) a schematic diagram of a multifunctional nucleic-acid-based anticancer drug, and (c) an image of an agarose gel indicating a complex of A10 aptamer/linear nucleic acid/doxorubicin and a complex of A10 aptamer-linear nucleic acid/doxorubicin.

The inventors completed the present invention by studying a multifunctional anticancer drug having a high targeting property and a high anticancer effect.

The present invention provides a multifunctional nucleic-acid-based anticancer drug prepared by physically capturing an anticancer drug in a linear nucleic acid having a thiol (—SH) group at the 5' end and then chemically binding gold nanoparticles with an aptamer, and a method of preparing the same.

As a result of tests using linear nucleic acid having various sequences to concentrate an anticancer drug at a high concentration, the inventors confirmed that 1 μM of a linear nucleic acid composed of a combination of DNA sequences of SEQ. ID. NOs: 1 and 2 can bind to a maximum of 10 μM of doxorubicin. An aromatic ring of the anticancer drug is inserted into the sequence of the linear nucleic acid, and particularly, a specific sequence (5'-CG-3' or 5'-GC-3') of the linear nucleic acid. The kind of the anticancer drug capable of binding to the linear nucleic acid of the present invention is not limited as long as it has an aromatic ring. The anticancer drug used herein is preferably doxorubicin, daunorubicin, mitoxanthrone, or epirubicin.

In addition, to develop an anticancer drug having a high targeting property, the inventors formed a doxorubicin-captured nucleic acid structure by binding a nucleic acid aptamer having a targeting property with a linear nucleic acid. The anticancer drug may be selectively delivered into cancer cells by binding the nucleic acid aptamer to the anticancer-drug-binding linear nucleic acid. Since the binding of the nucleic acid aptamer with the linear nucleic acid is performed by four overhangs, there is no limitation to the kind of an available nucleic acid aptamer having a cancer cell targeting property. That is, there is no limitation to the kind of a cancer to which the multifunctional nucleic-acid-based anticancer drug of the present invention can be used. The aptamer is preferably an A10 aptamer. The A10 aptamer is known to specifically bind to cells in which a prostate-specific membrane antigen (PSMA) is overexpressed among prostate cancer cells. Accordingly, the nucleic acid structure in which A10 aptamer-binding doxorubicin is captured may selectively deliver the anticancer drug to prostate cancer.

Since a thiol (—SH) is attached to the 5' end of the doxorubicin-captured nucleic acid structure and thus easily binds to gold nanoparticles by a covalent bond, the gold nanoparticles bind to the anticancer-drug-captured nucleic acid structure to prepare a multifunctional nucleic-acid-based anticancer drug. When the gold nanoparticles are irradiated with NIR rays, the temperature of the gold nanoparticles increases. In addition, it is known that cancer cells are more sensitive to temperature than normal cells, and therefore start to die at 42° C. or more. Accordingly, when the multifunctional nucleic-acid-based anticancer drug is irradiated with NIR rays, anticancer treatment using additionally generated heat is possible in addition to the anticancer drug included in the multifunctional nucleic-acid-based anticancer drug. In addition, due to the increased temperature of the gold nanoparticles, a release of the anticancer drug binding to the linear nucleic acid may be stimulated. In the present invention, using such a characteristic, multifunctional treatment using NIR rays and selective release of the anticancer drug is possible.

Figure 8:
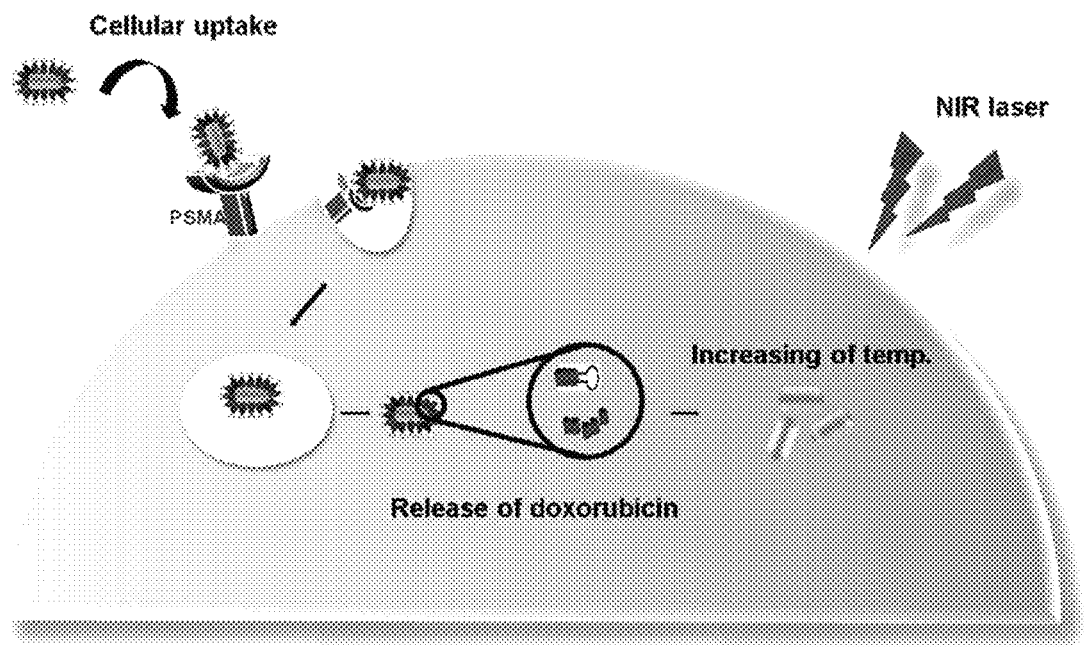
FIG. 8 is a schematic diagram of an action mechanism of a multifunctional nucleic-acid-based anticancer drug.

A schematic diagram of an action mechanism of the multifunctional nucleic-acid-based anticancer drug is shown in FIG. 8.

The A10 aptamer of the multifunctional nucleic-acid-based anticancer drug binds to PSMA-overexpressed prostate cancer cells, and thereby is delivered into the cells through endocytosis. The nucleic acid of the multifunctional nucleic-acid-based anticancer drug injected into the cells is degraded by all kinds of enzymes, and the anticancer drug (doxorubicin) binding to the nucleic acid is released. In addition, through NIR radiation, the temperature of gold nanoparticles is increased to stimulate the release of an anticancer drug, and cancer cells are effectively killed through thermal treatment.

In one example of the present invention, during the NIR radiation, it was confirmed that an emission amount of doxorubicin was increased due to an increase in temperature of the gold nanoparticles (refer to Example 4), and in another example, it was confirmed that the multifunctional nucleic-acid-based anticancer drug was delivered into prostate cancer cells due to the A10 aptamer (refer to Example 5). In still another example, it was confirmed that the multifunctional nucleic-acid-based anticancer drug effected both chemotherapy through the anticancer drug and thermal treatment through the nanoparticles, and thus could kill cells more effectively than a conventional anticancer drug (refer to Example 6).

According to the results, since the multifunctional nucleic-acid-based anticancer drug of the present invention has a cancer cell targeting property and a more excellent anticancer effect than the conventional anticancer drug, it is expected to be applied in treating various types of cancer. To this end, the present invention provides a pharmaceutical composition including an effective amount of the multifunctional nucleic-acid-based anticancer drug of the present invention.

The pharmaceutical composition of the present invention may include a pharmaceutically available carrier. The pharmaceutically available carrier may include saline, polyethyleneglycol, ethanol, vegetable oil, and isopropyl myristate, but the present invention is not limited thereto.

The present invention also provides a method of treating cancer by administrating a pharmaceutically effective amount of the pharmaceutical composition including the multifunctional nucleic-acid-based anticancer drug as an effective component to an individual. The term "individual" used herein refers to a subject having a disease to be treated, and more specifically, a mammal such as a human, a non-human primate, a mouse, a rat, a dog, a cat, a horse, or a cow. In addition, in the present invention, it is apparent to those of ordinary skill in the art that a range of the pharmaceutically effective amount can be controlled in various ways according to a patient's weight, age, sex, health condition, diet, administration time, administration method, excretion rate, and severity of a disease.

A preferable dosage of the multifunctional nucleic-acid-based anticancer drug of the present invention is dependent on the patient's condition and weight, severity of the disease, drug type, administration route, and duration, but may be suitably selected by those of ordinary skill in the art. However, the dosage is preferably 0.001 to 550 mg/kg, and more preferably 0.01 to 30 mg/kg. The drug may be administered once or several times a day. The multifunctional nucleic-acid-based anticancer drug of the present invention may be present in an amount of 0.0001 to 10 wt %, and preferably 0.001 to 1 wt % with respect to a total weight of the composition.

The pharmaceutical composition of the present invention may be administered to mammals such as rats, mice, livestock, or humans by various routes. There is no limitation to the administration method, and the pharmaceutical composition may be administered by oral, rectal, or intravascular administration, or muscular, subcutaneous, endometrial or intracerebroventricular injection.

Hereinafter, exemplary examples according to the present invention will be provided to help understanding of the present invention. However, the following examples are merely provided to more easily understand the present invention, and the scope of the present invention is not limited to the following examples.

Examples

Example 1

Manufacture of Multifunctional Nucleic-Acid-Based Anticancer Drug

To prepare a multifunctional nucleic-acid-based anticancer drug, an A10 aptamer (5'-TAGCGGGAGGACGAUGCGGAUCAGCCAUGUUUACGUCACUCCU-3' (SEQ ID NO: 3)) having a prostate cancer targeting property, and linear nucleic acids (5'-GCTACGAGTAGGTACGGATCTGGCTGTACTGATGTGCCTGCGAC-3' (SEQ. ID. NO: 1) and 5'-/thiol/GTCGCAGGCACATCAGTACAGCCAGATCCGTACCTACTCG-3' (SEQ. ID. NO: 2)) for capturing doxorubicin were used. The preparation of the A10 and the linear nucleic acid was entrusted to Integrated DNA Technology.

Figure 2:
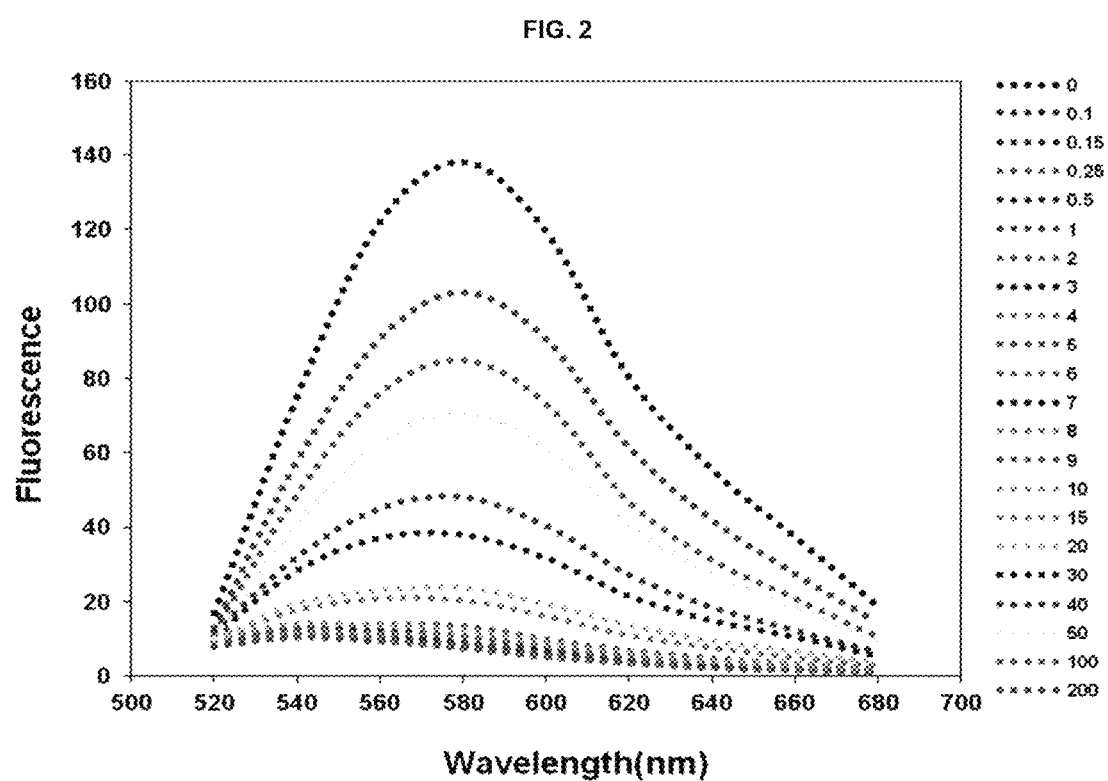
FIG. 2 is a graph showing results obtained by measuring autofluorescence of doxorubicin remaining in a solution after linear nucleic acid and doxorubicin are bound at various concentrations.

To prepare the doxorubicin-binding linear nucleic acid, the linear nucleic acid was mixed with doxorubicin in various concentrations (linear nucleic acid:doxorubicin=1:0.2 to 1:50), and the reaction was performed at room temperature for 24 hours. A supernatant was retrieved, and autofluorescence of the doxorubicin not binding to the linear nucleic acid was detected using a molecular device (SpectraMax M2 Microplate Reader). The results are shown in FIG. 2.

When the doxorubicin was captured in the linear nucleic acid, a concentration of the doxorubicin remaining in the solution was reduced, and the autofluorescence by the doxorubicin was also reduced. As shown in FIG. 2, it was confirmed that the doxorubicin ratio was reduced, a fluorescence intensity was reduced, and the fluorescence intensity was almost the same in the concentration ratio of 1:10 or less. The result shows that the maximum 10 μM doxorubicin was bound per 1 μM linear nucleic acid, and an optimal mixing ratio for preparing a linear nucleic acid/doxorubicin complex was 1:10.

Since the linear nucleic acid/doxorubicin complex and the A10 aptamer have four complementary terminal groups, they were bound to each other using a T4 DNA ligase, thereby forming an anticancer-drug-captured nucleic acid structure. To form the anticancer-drug-captured nucleic acid structure, the linear nucleic acid/doxorubicin complex was mixed with the A10 aptamer, reacted at room temperature for 12 hours, and identified through electrophoresis. The schematic diagram of the anticancer-drug-captured nucleic acid structure is shown in FIG. 1(a).

Since the linear nucleic acid has a thiol (—SH) at the 5' end, it is easily bound with the gold nanoparticles by a covalent bond. To bind the gold nanoparticles (10 nm×38 nm) with the anticancer-drug-captured nucleic acid structure, first, the gold nanoparticles were washed with nuclease free water five times through centrifugation to remove cetyl trimethylammonium bromide (CTAB) having cytotoxicity. In addition, the washed gold nanoparticles were mixed with the anticancer-drug-captured nucleic acid structure, and reacted at room temperature for 96 hours. During the reaction, to prevent agglomeration of the gold nanoparticles, the mixed product was dispersed using ultrasonic waves every 20 seconds. The prepared multifunctional nucleic-acid-based anticancer drug was centrifuged to separate unbinding anticancer-drug-captured nucleic acid structure and gold particles. The schematic diagram of the multifunctional nucleic-acid-based anticancer drug is shown in FIG. 1(b).

The prepared A10 aptamer, linear nucleic acid/doxorubicin complex, and multifunctional nucleic-acid-based anticancer drug were identified through electrophoresis using a 3% agarose gel. The results are shown in FIG. 1(c).

As shown in FIG. 1(c), it can be confirmed that the multifunctional nucleic-acid-based anticancer drug was larger than the A10 aptamer and linear nucleic acid/doxorubicin complex.

Example 2

Measurement of Amount of Nucleic Acid Structure in which Gold Nanoparticle-Binding Anticancer Drug was Captured To measure the amount of the nucleic acid structure in which the gold-nanoparticle-binding anticancer drug was captured, 260 nm of a supernatant of the reaction product was retrieved. The results are shown in FIG. 3.

Figure 3:
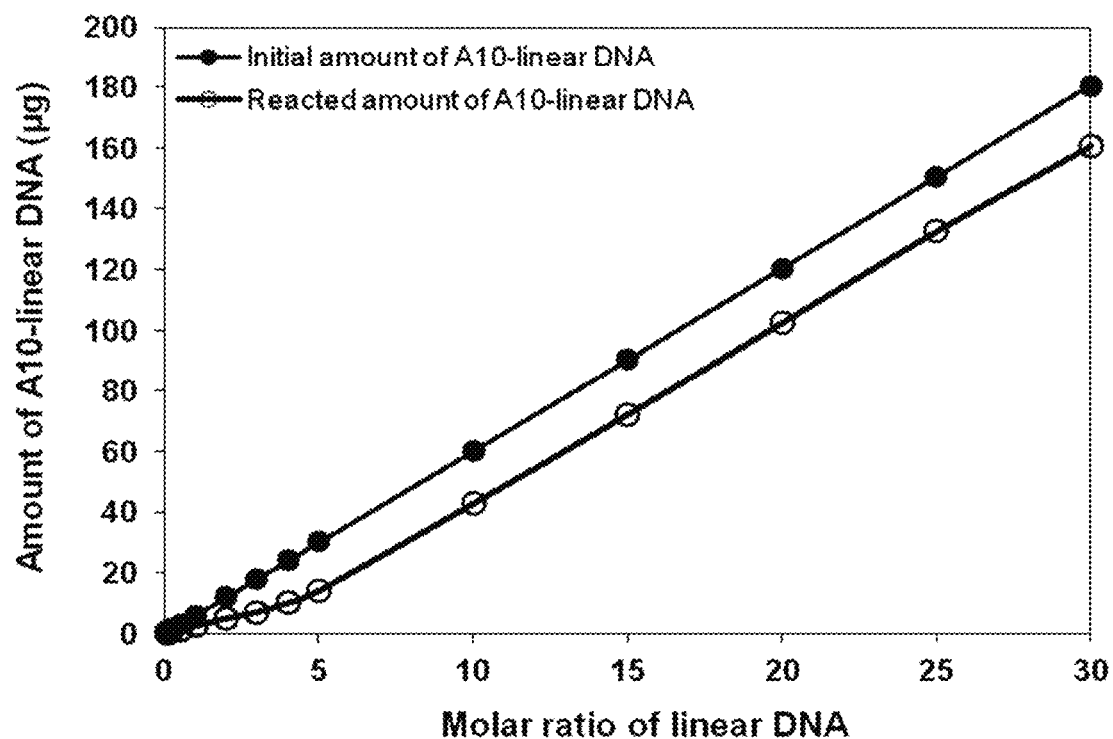
FIG. 3 is a graph showing results obtained by measuring an amount of a nucleic acid structure in which doxorubicin binding to gold nanoparticles at various concentrations is captured.

As shown in FIG. 3, it was confirmed that approximately 90% of the nucleic acid structures from the sample prepared by mixing 1 μM of the gold nanoparticles and 0.1 μM of the nucleic acid structure to the sample prepared by mixing 1 μM of the gold nanoparticles and 30 μM of the nucleic acid structure regularly bound to the gold nanoparticles. Since the 1 μM of the nucleic acid structure captured 10 μM of doxorubicin, when 1 μM of the gold nanoparticles was bound to 30 μM of the A10-doxorubicin-linear nucleic acid structure, an enormous amount of doxorubicin was included. In consideration of the maximum available amount of the drug and an amount of using the drug according to metastasis of cancer, the drug was expected to effectively treat prostate cancer cells.

Example 3

Measurement of Change in Temperature of Gold Nanoparticles

Figure 4:
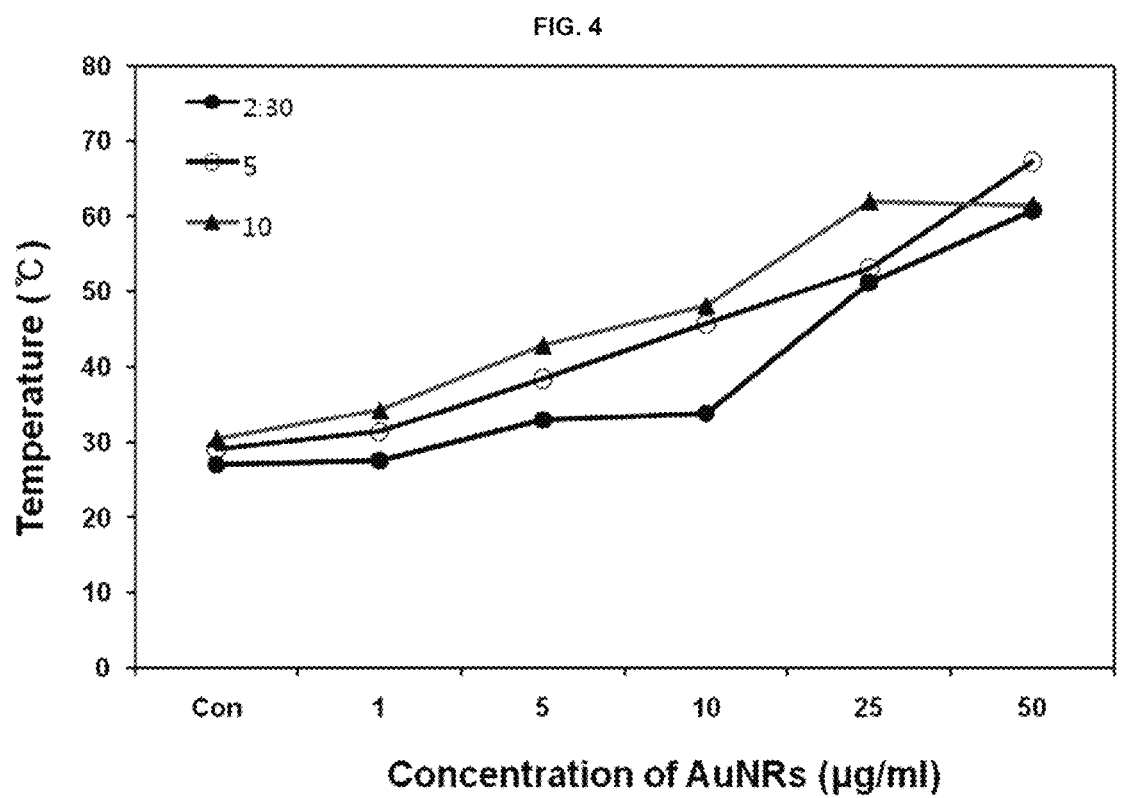
FIG. 4 is a graph showing results obtained by measuring change in temperature according to time and concentration when gold nanoparticles are irradiated with near-infrared (NIR) rays.

To measure the change in temperature according to NIR radiation of the gold nanoparticles, 1, 5, 10, 25 and 50 μg/ml of the gold nanoparticles were each irradiated with the NIR rays for 2 minutes and 30 seconds, 5 minutes, and 10 minutes, and then a temperature was measured using a probe thermometer. The results are shown in FIG. 4.

Cancer cells are more sensitive to temperature than normal cells, and thus start to die at 42° C. or more. It was confirmed that when 5 μg/ml of the gold nanoparticles was irradiated by NW radiation for 10 minutes, the temperature of the gold nanoparticles was increased to 42° C. The results indicate that when the multifunctional nucleic-acid-based anticancer drug reached the cancer cells to be treated in vivo, the cancer cells could be treated with heat generated by NIR radiation, in addition to treatment with the anticancer drug included in the multifunctional nucleic-acid-based anticancer drug.

Example 4

Measurement of Releasing Amount of Doxorubicin Through NIR Radiation

Figure 5:
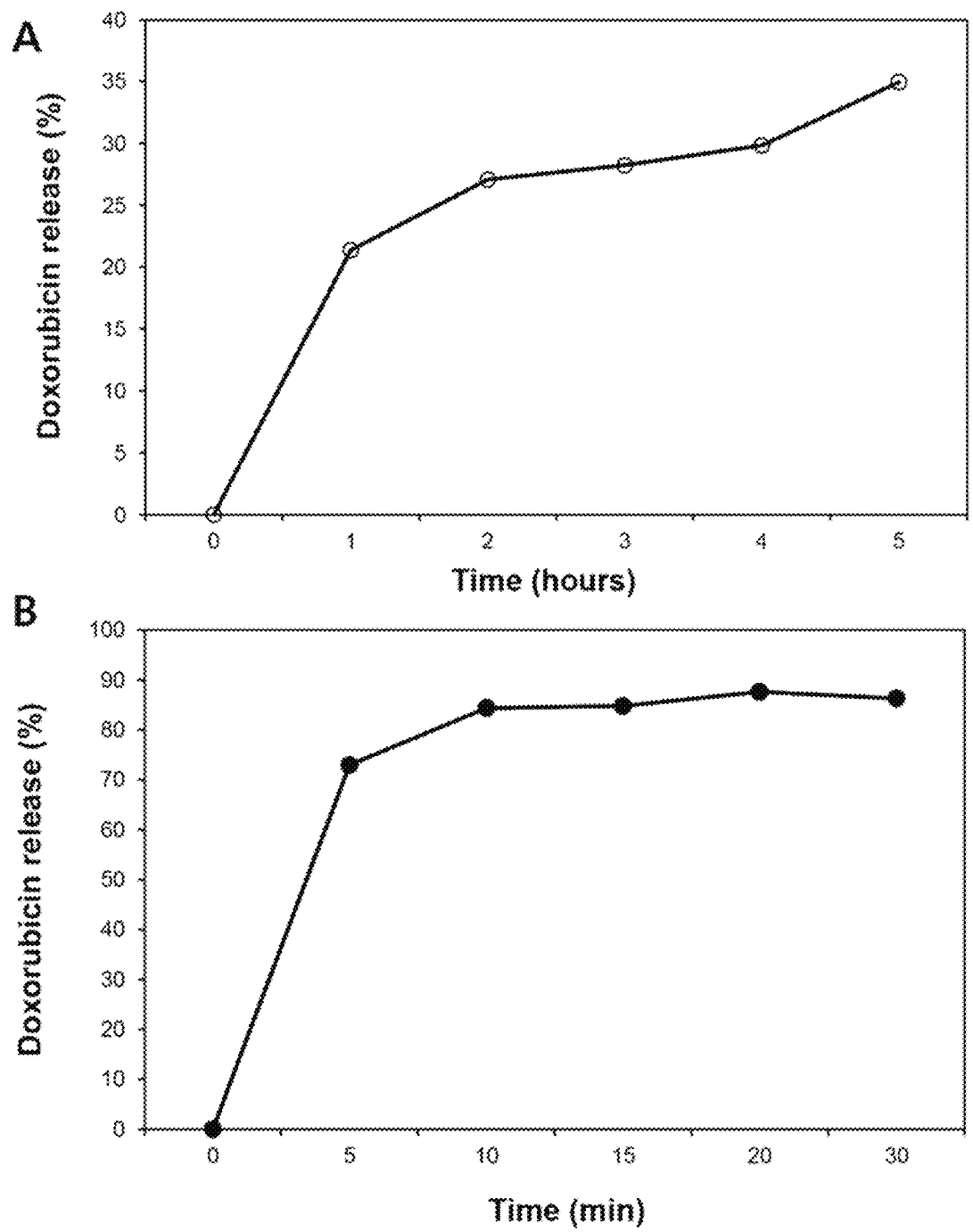
FIG. 5 is a graph showing results obtained by measuring a releasing amount of doxorubicin according to time when a multifunctional nucleic-acid-based anticancer drug is not irradiated (a) or irradiated (b) with NIR rays.

To confirm that the linear nucleic acid was partially dissolved by heat generated during the NIR radiation to facilitate the release of the doxorubicin, an amount of doxorubicin released after the multifunctional nucleic-acid-based anticancer drug was irradiated with NIR radiation was measured using autofluorescence. The results are shown in FIG. 5.

As shown in FIG. 5(a), it was confirmed that when the anticancer drug was not irradiated with the NIR rays, only 35% of the doxorubicin had been released after 5 hours, and when the anticancer drug was irradiated with the NIR rays, 80% or more of doxorubicin was released in only 5 minutes. The results indicate that when the multifunctional nucleic-acid-based anticancer drug reached cancer cells to be treated in vivo, the release of doxorubicin was stimulated by the NIR radiation to minimize an amount of doxorubicin remaining in the linear nucleic acid and increase treating efficiency.

Example 5

Confirmation of Intracellular Delivery of Multifunctional Nucleic-Acid-Based Anticancer Drug To confirm whether or not the multifunctional nucleic-acid-based anticancer drug was delivered into cells, prostate cancer cells (LNCaP cell line) were placed in a 96-well plate at a concentration of $1 \times 10^5$ cells, and cultured for 24 hours under conditions of 37° C. and 5% $CO_2$. In addition, after the cells were treated with 10 μM (concentration of the contained doxorubicin) of the multifunctional nucleic-acid-based anticancer drug for 2 hours, the medium was exchanged with a fresh RPMI 1640 medium to remove the multifunctional nucleic-acid-based anticancer drug remaining at an outside of the cells, and the resulting product was observed using a confocal microscope. The prostate cancer cells were stained with acridine orange. The results are shown in FIG. 6.

Figure 6:
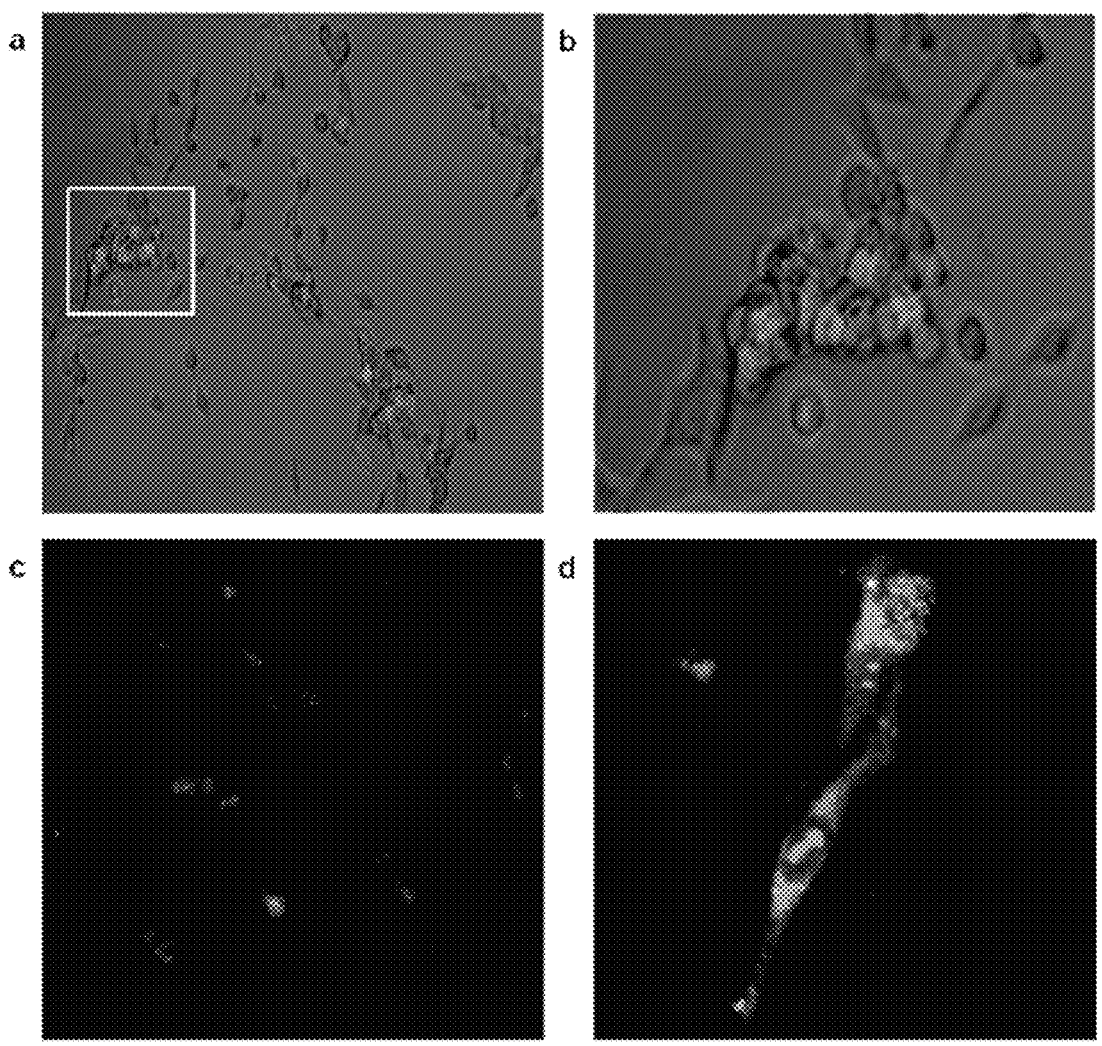
FIG. 6 is a confocal microscope image showing that a multifunctional nucleic-acid-based anticancer drug is delivered into prostate cancer cells.

As shown in FIG. 6, autofluorescence of the doxorubicin in the cells stained with the acridine orange was observed. The results mean that the multifunctional nucleic-acid-based anticancer drug was delivered into the cells by binding the A10 aptamer of the multifunctional nucleic-acid-based anticancer drug to a prostate-specific membrane antigen (PSMA), and the multifunctional nucleic-acid-based anticancer drug allowed the anticancer drug to be effectively delivered into desired cancer cells.

Example 6

Figure 7:
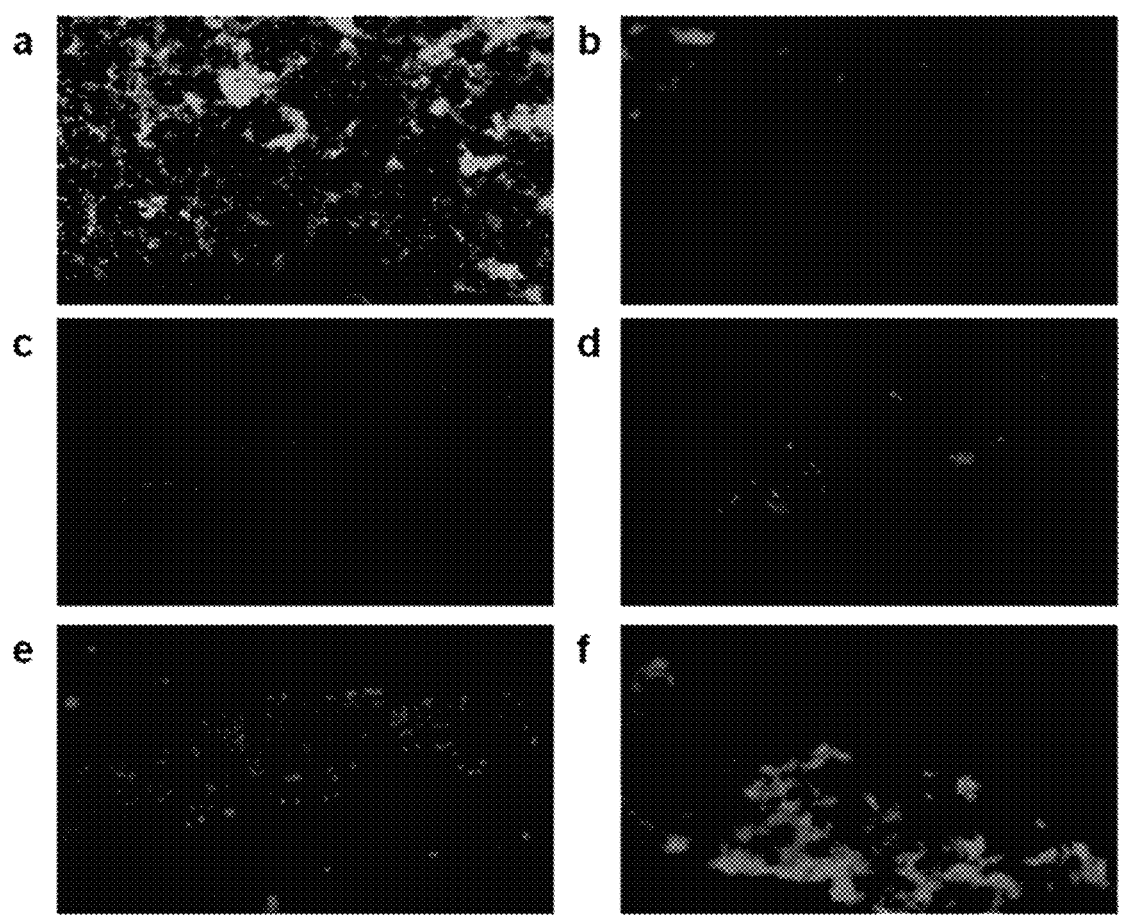
FIG. 7 shows confocal microscope images representing cell viability when prostate cancer cells are treated with (a) gold nanoparticles, (b) A10 aptamer/linear nucleic acid, (c) doxorubicin, (d) a nucleic acid structure in which doxorubicin is captured, and (e) a multifunctional nucleic-acid-based anticancer drug, and (f) a confocal microscope image of a negative control group (untreated)

Confirmation of Anticancer Effect of Multifunctional Nucleic-Acid-Based Anticancer Drug To confirm whether or not the multifunctional nucleic-acid-based anticancer drug had an anticancer effect, prostate cancer cells (LNCaP cell line) were placed in a 96-well plate at a concentration of $1 \times 10^5$ cells, and cultured for 24 hours under conditions of 37° C. and 5% $CO_2$. In addition, after the cells were treated with 10 μM (concentration of the contained doxorubicin) of the multifunctional nucleic-acid-based anticancer drug for 2 hours, the medium was exchanged with a fresh RPMI 1640 medium to remove the multifunctional nucleic-acid-based anticancer drug remaining at an outside of the cells, and the cells were cultured for 24 hours. Afterward, the cells were irradiated with NW radiation for 10 minutes, and stained with acridine orange and propidium iodide (PI). As a control group, instead of the multifunctional nucleic-acid-based anticancer drug, a test was performed using phosphate buffered saline, doxorubicin, gold nanoparticles, an A10 aptamer and an anticancer-drug-captured nucleic acid structure. The results observed by a confocal microscope are shown in FIG. 7.

In the case of the control group, the gold nanoparticles or linear nucleic-acid-treated cells, it was confirmed that since PI staining was not performed, red fluorescence was hardly observed. In the case of the cells treated with the doxorubicin, or the doxorubicin-captured nucleic acid structure, dead cells stained with PI were observed. Meanwhile, when the cells were treated with the multifunctional nucleic-acid-based anticancer drug, it was confirmed that most of the cells were stained with PI. The results indicate that the cells did not die due to the gold nanoparticles or linear nucleic acid, and were not stained with PI, which means that the gold nanoparticles or linear nucleic acid did not have cytotoxicity. Though the doxorubicin or the doxorubicin-captured nucleic acid structure can kill some cells, it is easily exposed to normal cells when applied in vivo, and thus can cause various side effects. This means that the multifunctional nucleic-acid-based anticancer drug can kill cells more effectively by applying both doxorubicin (chemotherapy) and an exothermic effect (thermal treatment). The results indicate that the multifunctional nucleic-acid-based anticancer drug has a more excellent therapeutic effect than the conventional anticancer drug.

A multifunctional nucleic-acid-based anticancer drug according to the present invention can deliver an anticancer drug into specific cells, stimulate thermal treatment and release of the anticancer drug due to gold particles, minimize an effect on normal cells due not only to its high targeting property but also to the fact that it is captured in a linear nucleic acid, have a better therapeutic effect than the conventional anticancer drug due to dual therapy of thermal treatment/chemotherapy, and freely introduce a nucleic acid aptamer or chemical having a targeting property suitable for treating various diseases to the multifunctional nucleic-acid-based anticancer drug. Therefore, the multifunctional nucleic-acid-based anticancer drug can be used in treatment of various intractable diseases.

While the invention has been shown and described with reference to certain exemplary embodiments thereof, it will be understood by those skilled in the art that various modifications in form and details may be made therein without departing from the spirit and scope of the invention as defined by the appended claims.

The invention claimed is:

1. A multifunctional nucleic-acid-based anticancer drug prepared by physically capturing an anticancer drug in a linear nucleic acid having a thiol group at the 5' end, and chemically binding gold nanoparticles and a nucleic acid aptamer, wherein the linear nucleic acid is composed of a combination of DNA sequences of SEQ. ID. NOs: 1 and 2.

2. The drug of claim 1, wherein the nucleic acid aptamer has a cancer cell targeting property.

3. The drug of claim 1, wherein the nucleic acid aptamer is an A10 aptamer selectively binding to prostate cancer cells.

4. The drug of claim 1, wherein the anticancer drug physically captured in the linear nucleic acid has an aromatic ring.

5. The drug of claim 1, wherein the anticancer drug physically captured in the linear nucleic acid is doxorubicin.

6. A method of preparing a multifunctional nucleic-acid-based anticancer drug, comprising:
   (a) capturing an anticancer drug in a linear nucleic acid having a thiol group at the 5' end, wherein the linear nucleic acid is composed of a combination of DNA sequences of SEQ. ID. NOs: 1 and 2;
   (b) forming an anticancer-drug-captured nucleic acid structure by binding a nucleic acid aptamer having a targeting property to the linear nucleic acid; and
   (c) binding gold nanoparticles to the anticancer-drug-captured nucleic acid structure.

7. The method of claim 6, wherein the step (a) is performed by inserting an aromatic ring of the anticancer drug into a sequence of the linear nucleic acid.

8. The method of claim 6, wherein the step (b) is performed by binding of complementary sequences of the linear nucleic acid and the nucleic acid aptamer.

9. The method of claim 6, wherein the step (c) is performed by a covalent bond between a thiol group of the anticancer-drug-captured nucleic acid structure and the gold nanoparticles.

10. A pharmaceutical composition comprising an effective amount of the multifunctional nucleic-acid-based anticancer drug of claim 1.

* * * * *

```
                        SEQUENCE LISTING

<160> NUMBER OF SEQ ID NOS: 4

<210> SEQ ID NO 1
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Linear nucleotide 1

<400> SEQUENCE: 1
gctacgagta ggtacggatc tggctgtact gatgtgcctg cgac                   44

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Linear nucleotide 2
<220> FEATURE:
<223> OTHER INFORMATION: 5'-thiol

<400> SEQUENCE: 2
gtcgcaggca catcagtaca gccagatccg tacctactcg                        40

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
tagcgggagg acgaugcgga ucagccaugu uuacgucacu ccu                    43

<210> SEQ ID NO 4
<211> LENGTH: 127
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
gtcgcaggca catcagtaca gccagatccg tacctactcg tagcgggagg acgaugcgga      60
ucagccaugu uuacgucacu ccugctacga gtaggtacgg atctggctgt actgatgtgc     120
ctgcgac                                                               127
```